(12) United States Patent
Klinkhammer et al.

(10) Patent No.: US 8,981,314 B2
(45) Date of Patent: Mar. 17, 2015

(54) METHOD AND APPARATUS FOR THE OPTICAL DETERMINATION OF TOTAL ORGANIC CARBON IN AQUEOUS STREAMS

(75) Inventors: Gary P Klinkhammer, Corvallis, OR (US); Paul H McClelland, Monmouth, OR (US); Don Jackson, Corvallis, OR (US); Chris J. Russo, Corvallis, OR (US)

(73) Assignee: Zaps Technologies, Inc, Corvallis, OR (US)

(*) Notice: Subject to any disclaimer, the term of this patent is extended or adjusted under 35 U.S.C. 154(b) by 528 days.

(21) Appl. No.: 13/370,213

(22) Filed: Feb. 9, 2012

(65) Prior Publication Data

US 2012/0205547 A1   Aug. 16, 2012

Related U.S. Application Data

(60) Provisional application No. 61/462,937, filed on Feb. 10, 2011.

(51) Int. Cl.
| | |
|---|---|
| *G01N 21/05* | (2006.01) |
| *G01N 21/33* | (2006.01) |
| *G01N 21/03* | (2006.01) |
| *G01N 21/27* | (2006.01) |

(52) U.S. Cl.
CPC ............ *G01N 21/33* (2013.01); *G01N 21/0303* (2013.01); *G01N 21/05* (2013.01); *G01N 21/276* (2013.01)
USPC .......................................... 250/372; 359/319

(58) Field of Classification Search
CPC ... G01N 21/31; G01N 21/33; G01N 21/8507; G01N 21/0303; G01J 1/429
USPC .......................................................... 250/372
See application file for complete search history.

(56) References Cited

U.S. PATENT DOCUMENTS

| | | | |
|---|---|---|---|
| 4,304,996 A | | 12/1981 | Blades |
| 5,304,492 A | * | 4/1994 | Klinkhammer ................. 436/52 |
| 5,364,492 A | | 11/1994 | Eckstein |
| 5,413,763 A | | 5/1995 | Jeffers |
| 5,567,621 A | * | 10/1996 | Tahara et al. ................. 436/103 |
| 6,444,474 B1 | | 9/2002 | Thomas |
| 7,411,668 B2 | | 8/2008 | Klinkhammer |
| 2003/0107012 A1 | * | 6/2003 | Cassidy et al. ................ 250/573 |
| 2009/0046287 A1 | * | 2/2009 | Haught et al. ................ 356/319 |

OTHER PUBLICATIONS

EPA: EPA Document #: EPA/600/R-051055, Method 415.3, "Determination of Total Organic Carbon and Specific UV Absorbance at 254nm in Source Water and Drinking Water", Rev. 1.1, Feb. 2005.
General Electric Company: "A Science Based Performance Comparison of On-Line TOC Analyzers" (2006).
Coble, P.G.,"Characterization of Marine and Terrestrial DOM in Seawater Using Excitation-Emission Matrix Spectroscopy", Mar, Chem., 51, 325-346, (1996).

(Continued)

*Primary Examiner* — Casey Bryant (57) ABSTRACT

A method and apparatus for the measurement of total organic carbon content in an aqueous stream is disclosed. Absorbance of electromagnetic energy by the aqueous stream is measured in an optical sample cell with pulsed light at a wavelength of 190 nm±10 nm. A value of total organic carbon from the measured absorbance is calculated without absorbance or fluorescence measurement at any other wavelength.

26 Claims, 6 Drawing Sheets

(56) References Cited

OTHER PUBLICATIONS

Sugimura, Y. and Suzuki, Y., "A high temperature catalytic oxidation method for the determination of non-volatile dissolved organic carbon in seawater by direct injection of a liquid sample", Mar. Chem., 24, 105-131. (1988).

Mopper, K. and Schultz, C.A., "Fluorescence as a possible tool for studying the nature and water column distribution of DOC components", Mar. Chem. 41, 229-238. (1993).

Zepp, R.G. and Schlotzhauer, P.F., "Comparison of Photochemical Behavior of Various Humic Substances in Water: III. Spectroscopic Properties of Humic Substances", Chemosphere 10, 479-486 (1981).

\* cited by examiner

METHOD AND APPARATUS FOR THE OPTICAL DETERMINATION OF TOTAL ORGANIC CARBON IN AQUEOUS STREAMS

The present disclosure claims the priority of U.S. Provisional Application No. 61/462,937, titled Method and Apparatus for the Optical Determination of Total Organic Carbon in Aqueous Streams filed on Feb. 10, 2011 by Klinkhammer et al., the contents of which are incorporated herein by reference.

The present invention relates to measurement of the purity of fluids and more particularly relates to a method and an apparatus for in situ analyses of fluids in real time.

BACKGROUND OF THE INVENTION

Total organic carbon (TOC) is a valuable measurement in environmental engineering and Earth sciences. The decay of the particulate fraction of TOC is the underlying process behind BOD (Biochemical Oxygen Demand) the most commonly regulated parameter for processed wastewater and industrial effluent. TOC is a fundamental parameter of water quality, summing both anthropogenic and natural pools of organic carbon compounds. TOC is also used extensively in the aquatic sciences as an indicator of biological activity. Total Organic Carbon, as used herein, is the concentration of all organic carbon compounds in a given sample, both dissolved and particulate. Organic carbon includes everything from decaying vegetation and live phytoplankton to man-made substances such as pharmaceuticals, pesticides, and Disinfection Byproducts (DBPs). Depending on the application, TOC concentrations of interest range from parts-per-billion to thousands of parts-per-million.

Because TOC is such a fundamental component of water quality assessment, there is a long and varied history of its measurement. The first widely-used automated determinations of TOC were made in the early 1970s with analyzers that used chemical oxidation to convert TOC compounds to carbon dioxide followed by measurement of the gas with Non-Dispersive Infrared (NDIR). Chemical oxidation was the standard method for breaking down TOC until a series of studies in the late 1980s found that the traditional chemical oxidation method did not always completely oxidize all TOC to $CO_2$. These findings led to a modified oxidation method involving the use of high temperature catalytic oxidation (HTCO). See "A High Temperature Catalytic Oxidation Method for the Determination of Non-Volatile Dissolved Organic Carbon in Seawater by Direct Injection of a Liquid Sample", Sugimura Y. and Suzuki Y., Mar. Chem., 24, 105-131 (1988). While the oxidation step in chemical oxidation and HTCO are different both techniques use NDIR.

Oxidative analyzers with NDIR detection remain the standard technology for measurement of TOC. While effective, this approach suffers from several shortcomings for long-term monitoring applications: (1) TOC analyzers require skilled operators and need a high level of maintenance and calibration. (2) These analyzers make extensive use of chemicals that are environmentally unfriendly and expensive. (3) Measuring TOC by analyzer is time-consuming and laboratories typically require several days to produce results. (4) The hardware used in this approach is cumbersome involving small-bore tubing and compressed gases. These requirements have made it difficult to modify the approach for continuous monitoring.

Direct optical measurement has the potential to alleviate or eliminate these problems and there have been multiple such approaches applied to monitoring TOC. Direct optical measurements normally focus on the ultraviolet part of the spectrum and can be grouped into fluorescence and absorption techniques.

Fluorescence is attractive because of its high sensitivity and relatively good S/N (signal to noise ratio) and there have been many studies relating the TOC of natural waters to the blue emission developed from UV excitation. See "Characterization of Marine and Terrestrial DOM in Seawater Using Excitation-Emission Matrix Spectroscopy", Coble, P. G., Mar, Chem., 51, 325-346, (1996). The term commonly used for TOC measured in this way is Fluorescent Dissolved Organic matter (FDOM). The FDOM parameter mimics TOC quite well in natural waters ranging between 0.5 and 5 mg/L, but the FDOM/TOC ratio varies with the type of organic matter. Marine organic carbon and terrestrial organic carbon, for example, have different fluorescence efficiencies and these differences complicate the FDOM-TOC relationship where these types mix—as in estuaries and the coastal ocean. FDOM is also broken down by sunlight (see, "Comparison of Photochemical Behavior of Various Humic Substances in Water: III. Spectroscopic Properties of Humic Substances", Zepp, R. G. and Schlotzhauer, P. F., Chemosphere 10, 479-486 (1981)) and this process of photo-oxidation further complicates the relationship with more conservative TOC. Moreover, anthropogenic organic compounds like pesticides often have complex cyclic structures that are generally more fluorescent than the straight-chain molecules that make up the bulk of natural organic matter. In summary, fluorescence works well as an analog for TOC in some cases but cannot be standardized for general use.

Organic compounds also absorb strongly in the UV and this absorption has also been exploited as an analog measurement for TOC. Differential absorbance spectroscopy, a measurement of water monitoring as a function of wavelength has been described previously. See "Development of Differential UV Spectroscopy for DBP Monitoring", Korshin, G. V., et al., AWWA Foundation, (2002). Monitoring TOC using UV absorption has focused on wavelengths between 200 and 400 nanometers where strong absorption bands of organic compounds occur. Historically this range also represented that part of the UV spectrum accessible by readily available optical components. However, absorptivity of water in this region of electromagnetic spectrum is a potential problem. Consider the plot of water absorptivity versus electromagnetic wavelength shown in the graph of FIG. 1 (derived from http://www.lsbu.ac.uk/water/vibrat.html#uv). The region of wavelengths between 200 nm and 400 nm is region of particular interest because it offers a window of minimum absorptivity of water. This means that UV light in this range penetrates relatively deeply into the water and enables a greater volume of water to be probed for materials. The net result is more scattering, and absorption measurements in this region are particularly sensitive to interference by particles in the water. It is well known that cyclic organic compounds absorb strongly in this region and that this specific absorption is centered at 254 nm. This property was developed into a water quality index called Specific UV Absorption or SUVA. SUVA is a measure of the relative aromaticity of the organic molecules in the organic carbon pool. Complex man-made hydrocarbons such as those present in pesticides and pharmaceuticals absorb more UV light than the simple long-chain molecules of natural origin. SUVA is calculated by normalizing UV absorption at a wavelength of 254 nm by the mass of organic carbon (see, EPA Document #: EPA/600/R-05/055, Method 415.3, "Determination of Total Organic Carbon and Specific UV Absorbance at 254 nm in Source Water and Drinking Water", Rev. 1.1, February 2005). In this way SUVA provides a qualitative measurement of the carbon pool that is particularly sensitive to artificial contaminants, where higher SUVA indicates water of lower quality. However, a greater volume of water being probed results in more scattering from that volume. Further, complex ring compounds tend to be strong absorbers and highly fluorescent thereby negating any simple relationship between TOC and fluorescence or UV absorption between 200 and 400 nm.

Particular issues exist with current instruments covering the UV-visual portion of the spectra. Because of the widely varying absorption coefficient of water, instruments employing a fixed path length measurement optical sample cell limits either absorption or the fluorescence signal.

Further, several relationships have been established in the art. The Beer-Lambert Law relates to absorbance readings. This is most often used in a quantitative way to determine concentrations of an absorbing species in solution: $A=\log_{10}(I_0/I)=\epsilon c L$, where A is the measured absorbance, $I_0$ is the intensity of the incident light at a given wavelength, I is the transmitted intensity, L the path length through the sample, and c the concentration of the absorbing species. For each species and wavelength, $\epsilon$ is a constant known as the molar absorptivity or extinction coefficient. This constant is a fundamental molecular property in a given solvent, at a particular temperature and pressure, and has units of 1/M*cm or often AU/M*cm.

The Beer-Lambert Law predicts a linear relationship between absorption and concentration and is useful for characterizing many compounds but does not hold as a universal relationship. A second order polynomial relationship between absorption and concentration is sometimes encountered for very large, complex molecules or simpler compounds at relatively high concentration. The Beer-Lambert law has implicit assumptions that must be met experimentally for it to apply. For instance, the chemical makeup and physical environment of the sample can alter its extinction coefficient. The chemical and physical conditions of a test sample therefore must match reference measurements for conclusions to be valid. The Beer-Lambert law also only applies to pure solutions and unencumbered absorbance. In the real world, scattering from particles and non-specific absorption contribute to measured values.

An apparatus for measuring the purity of fluids is known from the disclosure of U.S. Pat. No. 8,102,518 to Haught et al. Devices used for measuring fluid purity in general, and for identifying and quantifying the amount of impurities in particular, commonly use light as a probing mechanism. Such devices are generally referred to as photometers. A specific type of photometer is the spectrophotometer, which permits adjustment of the light frequency (i.e., wavelength), for making measurements at multiple frequencies. An optical sample cell contains a portion of fluid being analyzed at any given moment.

Electromagnetic energy that is used to irradiate the aqueous stream may either be reflected by material in the aqueous stream, transmitted through the aqueous stream and its material load, or absorbed by the aqueous stream material. In the instance where the electromagnetic energy is absorbed by the aqueous stream material, the aqueous stream material may also fluoresce. In devices used to measure purity, one of three basic measurement methodologies following from these potential interactions of the electromagnetic energy with the aqueous stream is generally employed. These methodologies measure the parameters absorption, reflectance, and fluorescence of the aqueous stream in the optical sample cell. In accomplishing the various methodologies, an electromagnetic energy detector has been disposed with respect to an electromagnetic energy transmitter so that the detector is optimally positioned to be responsive to the associated parameter.

It is desirable, then, for an apparent real time view of the TOC in an aqueous sample to be obtained from observations available in intervals of seconds or minutes and not the hours or days traditionally obtained from laboratory tools such those recommended in the SUVA specification.

DETAILED DESCRIPTION OF THE EMBODIMENTS

As stated above, current techniques for determining Total Organic Carbon (TOC) have the disadvantages of particles disposed in an aqueous sample scattering the illumination probe (typically an illumination at 254 nm) and of the strong absorption of complex carbon ring compounds at 254 nm negating a simple mathematical relationship between a measured absorption value and a TOC value.

Figure 1:
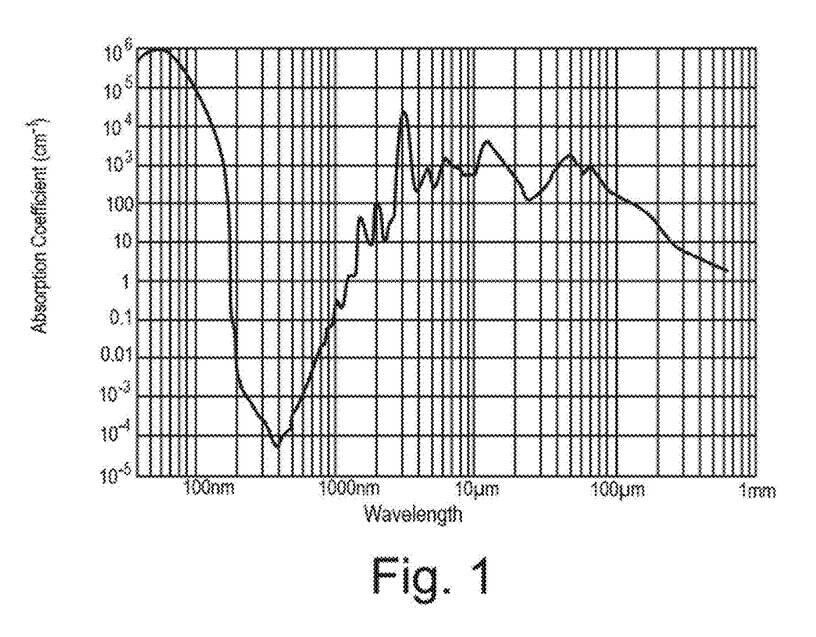
FIG. 1 is a graph of electromagnetic wavelength versus absorption coefficient, with the plot showing the absorption coefficient of pure water, derived from the work of Dr. Martin Chaplin, Emeritus Professor of Applied Science, London South Bank University.

It is readily observable from the absorption coefficient curve of FIG. 1 that the absorption of electromagnetic energy by the H—O bonds of water climbs steeply with wavelengths less than 200 nm. The transparency of water diminishes quickly and wavelengths less than 200 nm have generally been avoided by previous TOC-related measurements at least because of this steep slope. However, it has been found that electromagnetic energy in the region between 180 nm and 200 nm of the deep UV spectrum vibrates C—H and C—O bonds, making this region a viable region for absorption measurements useful for TOC calculations. Moreover, the region of 180 nm to 200 nm is less affected by trace concentrations of complex organics, colloids and particles than other accessible regions of the UV spectrum, which makes absorption measurements at 193 nm generally more stable with better signal-to-noise (S/N). The higher electromagnetic energy in this range (as compared to the conventional 254 nm energy) more vigorously vibrates organic carbon in particulate organic matter, for example algae cells, which can be a significant part of the TOC pool in natural water systems. Thus, there is an engineering trade-off between greater water absorption and an improved S/N of the desired absorption signal of organic carbon.

Previous absorption measurements leading to the calculation of TOC, typically performed at a wavelength of 254 nm, required one or more ancillary measurements to obtain values for particulates disposed in the aqueous sample and for complex carbon compounds, which interfered with the calculation of TOC. Typically, a measurement of turbidity is made at an illumination probe excitation wavelength of 320 nm and a detection of resulting fluorescence is made at a wavelength of 430 nm. And a second measurement of absorbance is made at a wavelength of between 600 nm to 700 nm for scattering estimation. The detection of such ancillary signals is used in a complex calculation to remove the interference effect upon the absorption measurement at 254 nm. This corrected absorption value is then used in the calculation of TOC.

An embodiment of the present invention utilizes an illumination probe of electromagnetic energy having a wavelength of 193 nm and a filtered detection of absorbance of an aqueous sample solution at the same 193 nm. No other correction measurements are taken at other wavelengths and the Beer-Lambert Law is directly solved for concentration.

The accepted standard for conventional TOC analysis in clean water applications is potassium hydrogen phthalate (KHP). When absorption measurements at 193 nm are calibrated with KHP and these concentrations compared with those determined by standard NDIR (non-dispersive infrared) analyzers they agree within analytical precision. This consistency makes it possible to directly compare TOC levels determined by continuous optical measurements at 193 nm with those determined by laboratory analysis. There are issues related to TOC measurements at 193 nm and these relate to difficulties in attaining an adequate photon flux due to absorption by water, and large deviations from the Beer-Lambert Law above 20 mg/L. These limitations require high light input or a means of varying the path length in order to ensure good photon counting statistics and a high quality calibration to maintain accuracy.

Figure 2:
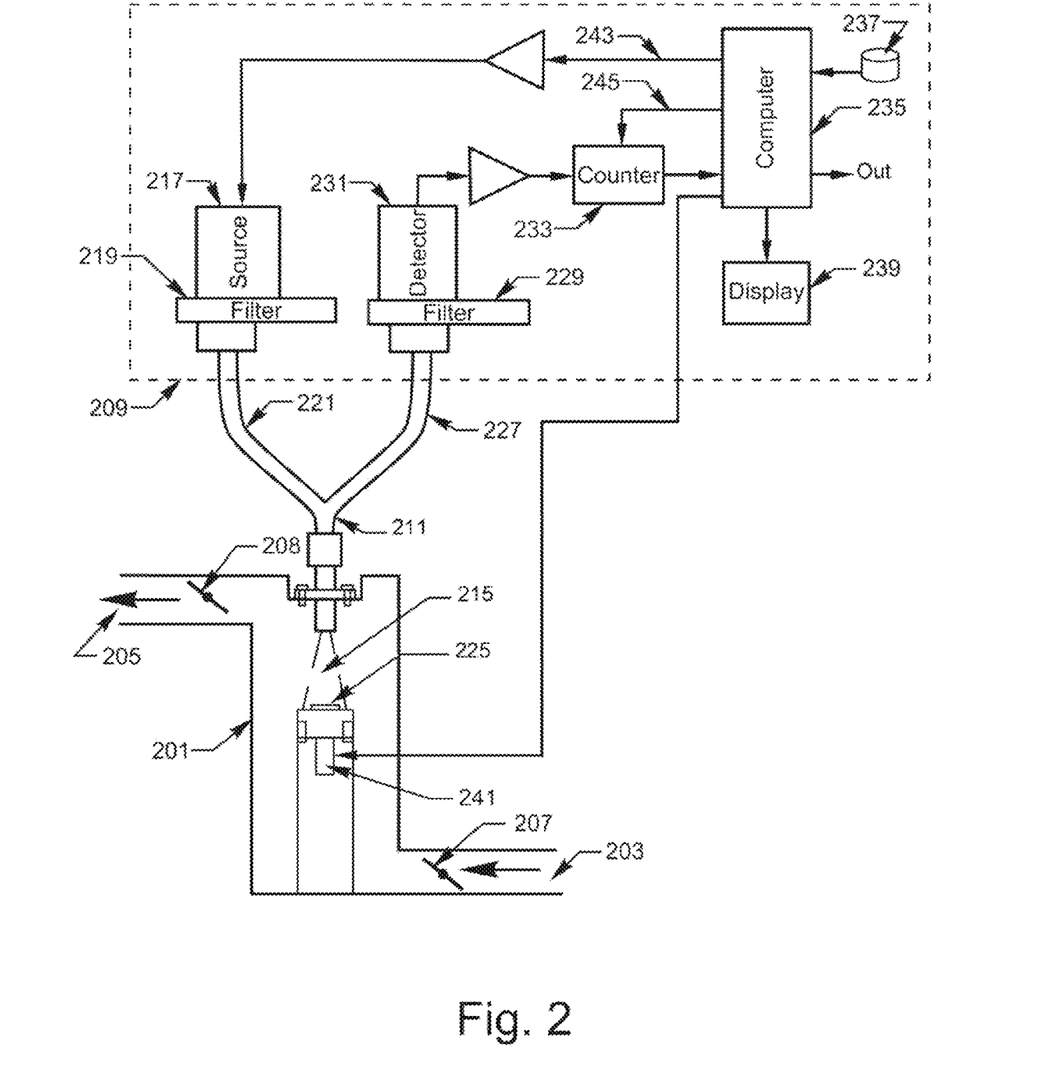
FIG. 2 is a block diagram of an analytical instrument for the determination of total organic carbon, which may be employed in the present invention.

An embodiment of an analytical instrument for the determination of total organic carbon, which may employ the present invention, is shown in the diagram of FIG. 2. An optical sample cell 201 is caused to contain an aqueous sample to be analyzed. In an embodiment of the present invention, an aqueous sample is caused to flow through the optical sample cell 201 from inlet 203 to outlet 205. Valves 207, 208 are controlled to regulate the flow rate of aqueous stream through the optical sample cell, particularly if the stream is to be intermittent, reduced, or combined at certain times. Optical components and electronics 209 are optically connected to the optical sample cell through an optical fiber bundle 211. A narrowband electromagnetic energy source for supplying an illumination probe 215 to the aqueous stream, in an embodiment employing the present invention utilizes a source 217 of electromagnetic energy such as a flash lamp. Light (a portion of electromagnetic radiation occurring within wavelengths including infrared, visible light, and ultraviolet light) is directed by the system through a bandpass optical filter 219 to select a desired wavelength and passed into and through a portion 221 of optical fiber assembly 211 to the optical sample cell 201. The light is then directed, as the illumination probe 215, through the aqueous sample in the optical sample cell 201 and reflected from a light reflector 225 disposed in the optical sample cell, through the aqueous sample again, and back into the optical fiber bundle 211. A separate portion 227 of the optical fiber bundle 211 directs the returning light through another bandpass optical filter 229 and is detected by an optical detector 231.

Signals from detector 231 are coupled to a counter 233 and then to a computer 235. Computer 235 may be, alternatively, a programmed general-purpose computer or a specialized computer controller to control the movement of positioning motor 241, valves 207, 208, optical filters, etc. Signals from the optical detector 231 are received, recorded and analyzed by the computer 235 and the results are stored in a memory 237, reported on a display 239 or output to external devices, or signals are fed back to affect appropriate change in the sensor system or fluid control system as a feedback loop. Further, algorithms stored in memory 237 are recalled and executed by computer 235 to extract useful information from the data collected.

Figure 3:
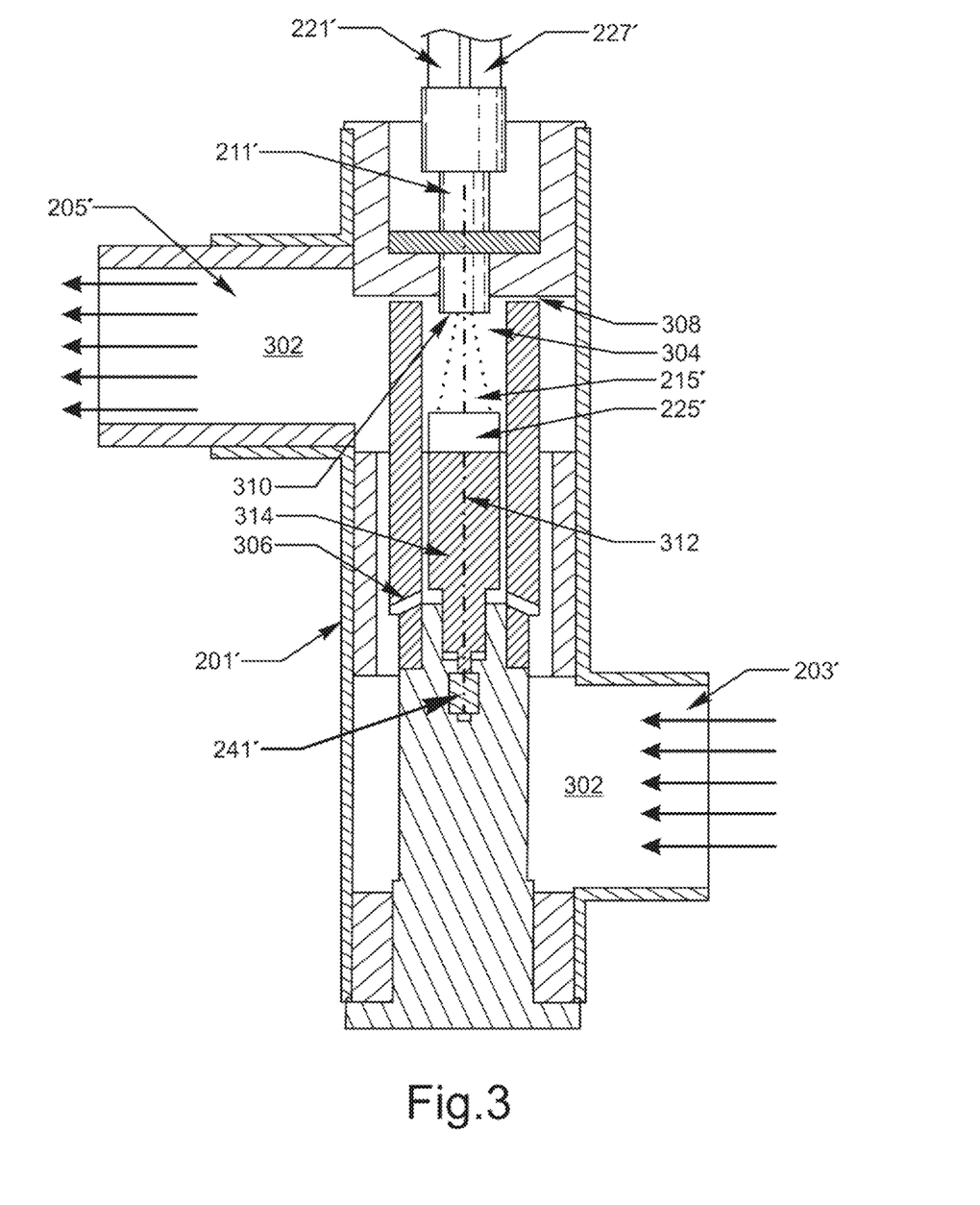
FIG. 3 is a cross sectional drawing of an optical sample cell for measuring the purity of fluids, which may be employed in the present invention.

An exemplary cross section of an optical sample cell is depicted in the diagram of FIG. 3. An optical sample cell 201' is shown in cross section. Optical fiber portions 221' and 227' of optical fiber bundle 211' provide for two directive optical paths, conducting electromagnetic energy emitted from filtered electromagnetic source to an interior chamber 302 of the optical sample cell 201', and conducting electromagnetic energy from the chamber 302 to the electromagnetic detector. The chamber 302 includes an inner flow tube 304 that, in turn, encompasses the reflective element 225'. The inner flow tube 304 includes one or more apertures 306, at a first end of the inner flow tube 304 through which an aqueous sample enters the tube, and one or more apertures 308 at a second end of the inner flow tube through which the aqueous sample exits the tube. Respective side openings 203', 205' of the optical sample cell 201' provide for aqueous sample inlet and aqueous sample outlet. An aqueous sample flowing through the chamber envelops the reflective element 225' and the common end 310 of the bifurcated optical fiber bundle 211'. Electromagnetic energy enters the aqueous sample from the common end 310 of the optical fiber bundle 211'. The reflective element 225' returns the electromagnetic energy through the aqueous sample, back into the common end 310 and thence to the detector.

The electromagnetic energy source in one embodiment is a light source with output wavelengths in the range from 1000 nm to at least 180 nm and capable of between 10 and 100 pulses per second (Hz) operation with timing control. A pulsed xenon source is an example of such a light source. The bifurcated fiber optic bundle 211' places a beam of electromagnetic energy, an illumination probe 215', along the optical axis 312 of the flow-thorough optical sample cell 201'. The reflective element 225' intersects the optical axis 312 and returns the illumination probe 215' toward an optical output port, the common end 310, of the optical fiber bundle 211', reilluminating the aqueous sample. The optical fiber portion 227' of optical fiber bundle 211' routes the reilluminating probe electromagnetic energy to the photon detector 231, which has electromagnetic energy sensitivity from at least 180 nm to 200 nm. In one embodiment an optical bandpass filter 229 is coupled between optical fiber portion 227 and the detector 231 and provides a filter bandpass of 180 nm to 200 nm. Detections by detector 231 are coupled to the computer 235 and provides instrument control and computation of the total organic carbon concentration in the sample volume traversed by the illumination probe. An associated memory 237 stores a sequence of steps forming an applications program for execution by the computer 235 and stores the data from the detector. A feature of this embodiment, shown in FIG. 2, is a local and remote data access portal, "output". A further feature of this embodiment is the ability to adjust the optical sample cell illumination probe path length with motor 241 to at least 3 preset lengths under control of the computer without manual intervention.

The length of the path traversed by the illumination probe 206 is adjustable such that the concentration range of the analysis instrument measurement may be increased (by varying the value L of the Beer-Lambert Law calculation). In an embodiment of the present invention, the reflective element 225' is mounted on a movable piston 314, which translates along the optical axis 312 toward and away from the illumination input port and illumination output port 310 of the optical sample call 201'. The translation of piston 314 is realized by a precision stepping motor 241', manufactured by Anaheim Automation, Inc., which carefully tracks to a precision of 20 parts per million (ppm). In this embodiment motor 241' is disposed within the optical sample call 201'. The path length of the illumination probe 215' is varied from a length of 0.2 cm to 10.0 cm, including the illumination incident path through the aqueous sample from input port 310 to the reflective element 215' and the reillumination path returning through the aqueous sample from the reflective element 215' to the output port 310. Motor 241' is energized and controlled by the computer 235, which factors the known position of piston 314 as an illumination probe path length into the TOC calculation.

One feature of an embodiment of the present invention is that the illumination of the aqueous sample cell 201 is pulsed, or strobed, periodically so that a significant number of absorption samples are taken during one measurement event. The more samples that are taken, the more the TOC measurement error is reduced. Although one embodiment employs periodic strobing for simplification of synchronization, aperiodic strobing may alternately be employed.

Referring again to FIG. 2, the illumination source 217 is caused to flash for a brief period of time by a strobe pulse 243 derived from computer 235. In an embodiment, the illumination source 217 delivers a light pulse lasting a duration of 0.4 μsec to 0.8 μsec. This light pulse width may be adjusted depending upon the type of illumination source implemented and the aqueous sample conditions, among other variable conditions. In some instances where the illumination source is not well suited for strobe operation, optical filter 219 may further include a mechanical chopper, a Q-switched cell, or other light-interrupting device to provide a pulsed light output. The periodicity of the pulses in an embodiment is 100 Hz, but may range from about 10 Hz to about 1000 Hz, as long as the illumination source can strobe at these rates and synchronization with the detector can be maintained.

Following transit of the optical sample cell 201, the illumination probe is collected by optical filter bundle 211 and routed to the optical bundle portion 227. The collected illumination probe is filtered by optical bandpass filter 229 to pass the 190 nm±10 nm wavelength light to a sensitive electromagnetic energy photon detector 231. This detector 231 provides an output equivalent to a count of electromagnetic energy photons and is realized in one embodiment with a Excelitas Technologies Corporation PM962 photon counting module. Other devices may be substituted but should be limited in their noise generation to a background noise count rate of fewer than 100 counts/sec, and preferably fewer than 20 counts/sec. A pulse counter 233 receives an enabling gating command 245 from computer 235 to commence a count window, during which photon detections are accepted from detector 231. In one embodiment, the count window is 10 msec in duration, synchronized to commence a short time delay before the strobing of source 217. The count window may, however, be lengthened or shortened depending upon operating conditions. The 190 nm±10 nm wavelength light illumination probe detector and photon counting arrangement is expected to have a minimum capability of $5 \times 10^6$ counts/sec and preferably has a count capability of $20 \times 10^6$ counts/sec.

Figure 4:
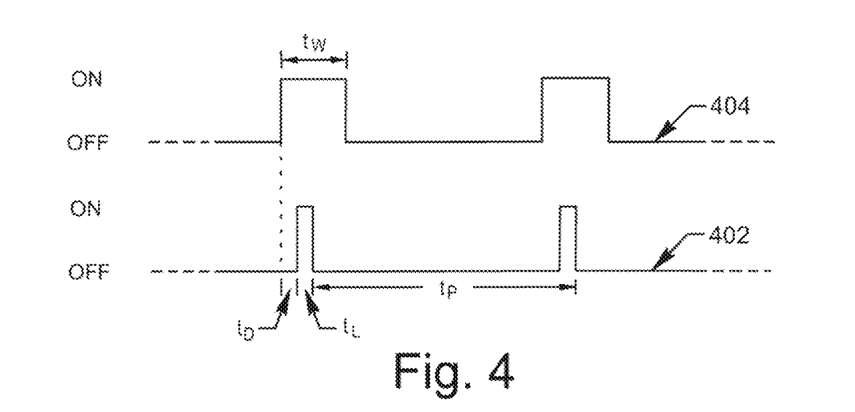
FIG. 4 is a timing diagram of optical measurements, which may be employed in the present invention.

Operation of the apparatus can be perceived in the timing diagram of FIG. 4. The lower curve 402 represents the timing of the strobed illumination pulses into the optical sample cell 201 from the illumination source 217 and filter 219. The illumination pulse duration, $t_L$, is timed to last 0.4 μsec to 0.8 μsec in one embodiment. The repetition rate, or periodicity, $t_P$, is 100 msec (100 Hz) in that embodiment. The upper curve 404 represents the timing of the count window, which commences prior to a short delay, $t_D$, preceding the synchronized illumination source pulse, and further illustrates the duration of the timing window, $t_W$. A TOC measurement event typically occurs for a time period of between two and eight seconds, after which accumulated data are processed by the computer 235 and output to local storage 237 and to remote devices controlling the aqueous stream or to remote monitoring and data collection devices. Computer 235 also provides a display for on-site operator monitoring of TOC measurements via display 239, which permits, among other things, viewing of the results of the last measured value of TOC.

Operationally, the apparatus measuring TOC makes such a measurement on-site and in real-time. This advancement in the art is enabled by the use of the near UV electromagnetic energy at 190 nm±10 nm and pulsed light measurement. The computer includes a stored operating system and software application programs formed of program code that define algorithms and which can be implemented as computer executable code modules that can be stored on computer readable media, read by one or more processors, and executed thereon. The operating system and the programs are executed by the computer during operation of the apparatus. In addition, separate boxes or illustrated separation of functional elements of illustrated systems does not necessarily require physical separation of such functions, as communications between such elements can occur by way of messaging, function calls, shared memory space, and so on, without any such physical separation. A person of ordinary skill would be able to use the present description to produce implementations and embodiments on different physical platforms or form factors without deviating from the scope of the claims and their equivalents.

Figure 5:
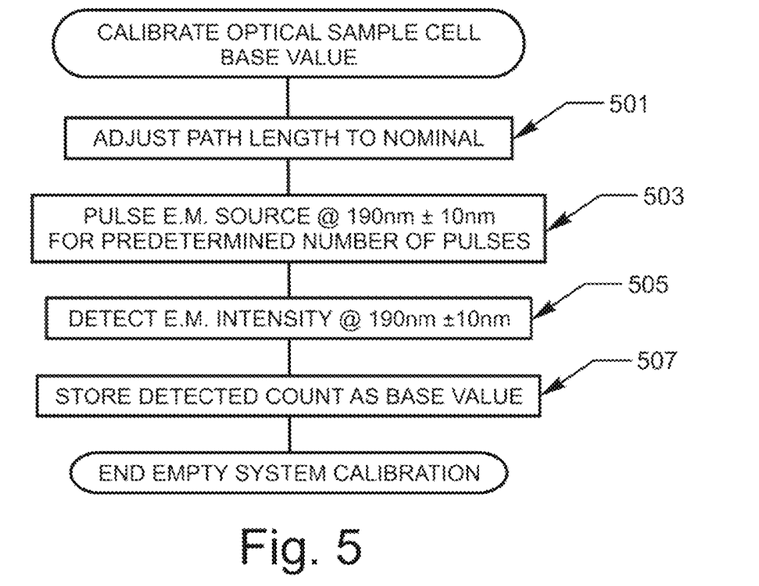
FIG. 5 is a flowchart of a process of empty system calibration, which may be employed in the present invention.

The optical sample cell and supporting equipment is first calibrated to account for equipment variation, aging, and cleanliness. As illustrated in the flow diagram of FIG. 5, the illumination probe path length, as established by the position of the reflecting element 225', is set to nominal, at 501. The electromagnetic energy source is energized for a predetermined number of pulses at a wavelength of 190 nm±10 nm, at 503. The count window is synchronously opened and the electromagnetic energy intensity, in the form of a photon count representation, is measured during the duration of the count window, at 505. The detected count, processed over the predetermined number of pulses, is stored in memory 237 as the base value, at 507. This empty-system calibration is performed at the factory, often at installation, and at relatively rare instances thereafter. It establishes base values for signal-to-noise, counting variations, and maximum counts.

Figure 6:
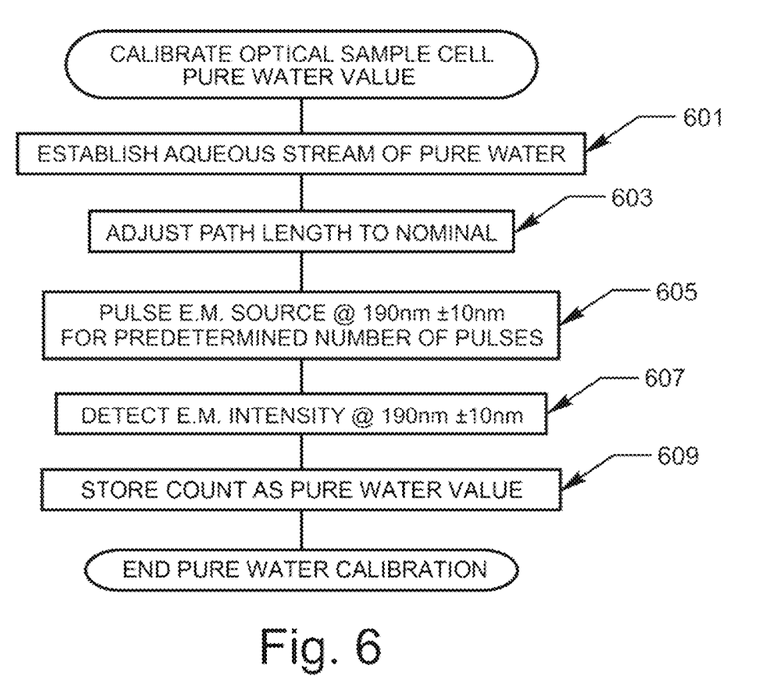
FIG. 6 is a flowchart of a process of water zero calibration, which may be employed in the present invention.

A calibration photon count by the apparatus is obtained for a stream of pure water (pure water is defined in EPA Document #: EPA/600/R-05/055, Method 415.3, "Determination of Total Organic Carbon and Specific UV Absorbance at 254 nm in Source Water and Drinking Water", Rev. 1.1, February 2005, paragraphs 6.4 and 7.2). This photon count establishes the "pure-water" value, count variation rate, absorption and scattering characteristics of water in the optical sample cell, and optical sample cell behavior at the 190 nm±10 nm wavelength. A process is illustrated in FIG. 6. An aqueous stream of pure water is established through the optical sample cell

201, at 601. The illumination probe path length is set at the nominal length, at 603, and the electromagnetic energy source 217 is energized to pulse light at 190 nm±10 nm for a second predetermined number of pulses, at 605. The count window is synchronously opened and the electromagnetic intensity, in the form of a photon count representation, is measured by detector 231 and counter 233 during the duration of the count window, at 607. The detected count, processed over the predetermined number of pulses is stored in memory 237 as the pure-water value, at 609. The pure-water calibration value is established at the factory, upon installation, and on a more frequent basis than the base value. Photon counts of the installed system, when connected to cleaning/flush water, are compared to the stored pure-water value and system offsets are applied that allow tracking of the apparatus performance independent of the intended measurements. Thus, the apparatus "knows" when to flush the optical sample cell and when manual cleaning is needed due to the light path not performing as expected.

Figure 7:
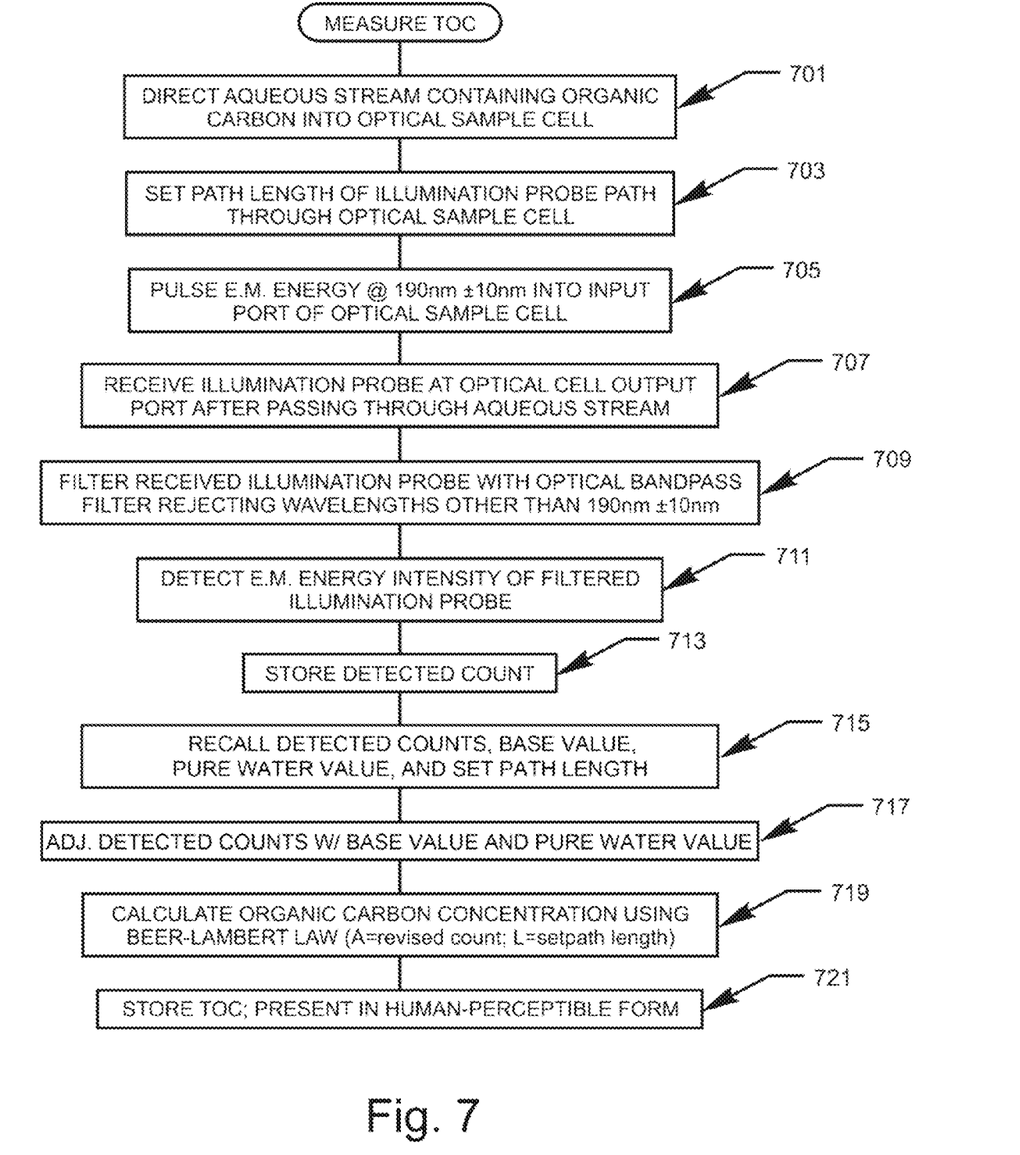
FIG. 7 is a flowchart of a process of TOC measurement, which may be employed in the present invention.

Total organic carbon (TOC) is measured with an electromagnetic energy source having a long, stable output, a very low noise photon counting arrangement, the optical sample cell, and data processing. With only one source and one detector arrangement operating at one wavelength, the amount of data scatter is lower and can be tracked from the apparatus throughout its operational life. The measurement of TOC in one embodiment is shown in the flowchart of FIG. 7. An aqueous stream to be measured is directed into the optical sample cell 201, at 701. The illumination probe path length is set in accordance with a distance suitable for photon counting of samples of the type being measured, i.e., a nominal path length, at 703, and electromagnetic energy is generated and strobed for a number of pulses into the input port of optical sample cell 201 at a wavelength of 190 nm±10 nm for a time of, for example, 2-10 seconds, at 705. The returning illumination probe is received at the optical sample cell 201 output port 310 after passing through the aqueous stream, at 707, and filtered by bandpass filter 229 to reject wavelengths other than 190 nm±10 nm, at 709. The count window is synchronously opened for each pulse and the electromagnetic intensity of the returning illumination probe, in the form of a photon count representation, is measured by detector 231 and counter 233 during the duration of the count window, at 711. The detected count for each light pulse during the count window is stored in memory 237, at 713. At the conclusion of the measurement event, which in one embodiment may be 2 seconds to 10 seconds, the set of counts, the base value, the pure-water value, and the path length are recalled from memory 237 by the computer 235, at 715. The photon counts are adjusted with the base value and the pure-water value, at 717, and a concentration of organic carbon is calculated by the computer using Beer-Lambert Law, with A=adjusted photon count representation and L=path length, at 719. The value of the calculated TOC is locally stored at memory 237, presented to the human operator on a display 239, and output to other devices for storage, analysis, and process control of the system generating the aqueous stream, at 721.

As an alternative to the xenon-flash light source, a low pressure mercury vapor lamp may be employed. Such an electromagnetic energy source generates light at least at the wavelengths of 185 nm, 254 nm, and 312 nm. The 185 nm wavelength is of particular interest for application in an alternative embodiment. The 185 nm wavelength is filtered from the low pressure mercury lamp and utilized as the source of illumination.

Thus, an apparatus and method for in situ analysis of total organic carbon in real-time has been shown and described.

Figure 8:
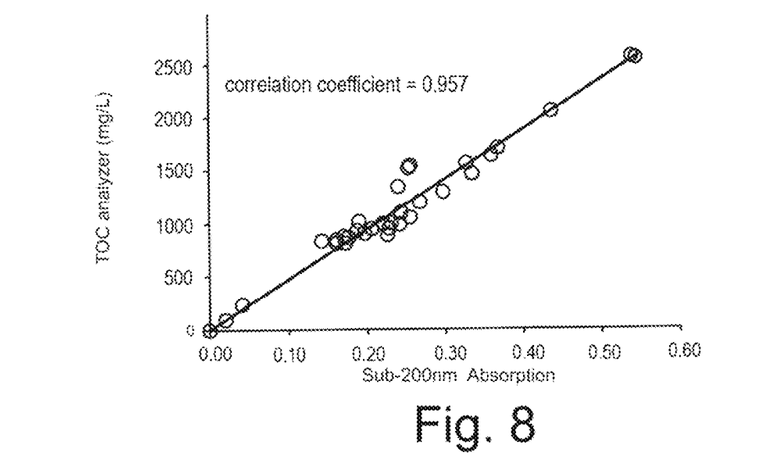
FIGS. 8, 9, and 10 are graphs of measurements made employing an embodiment of the present invention.
Figure 9:
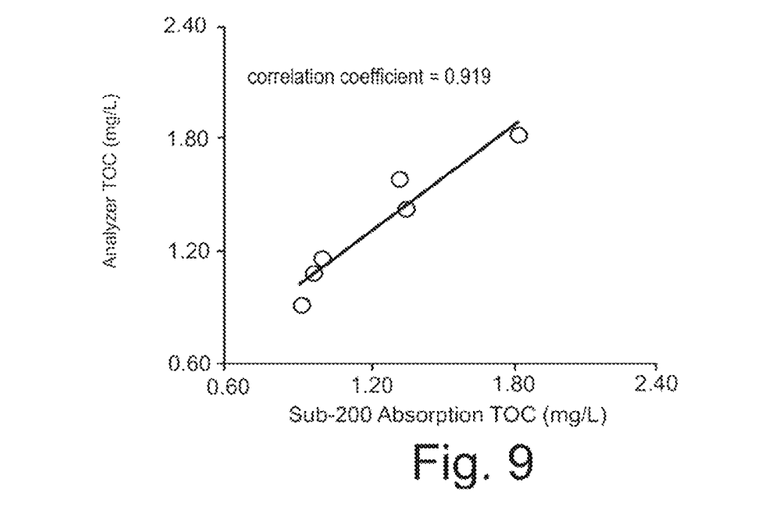
Figure 10:
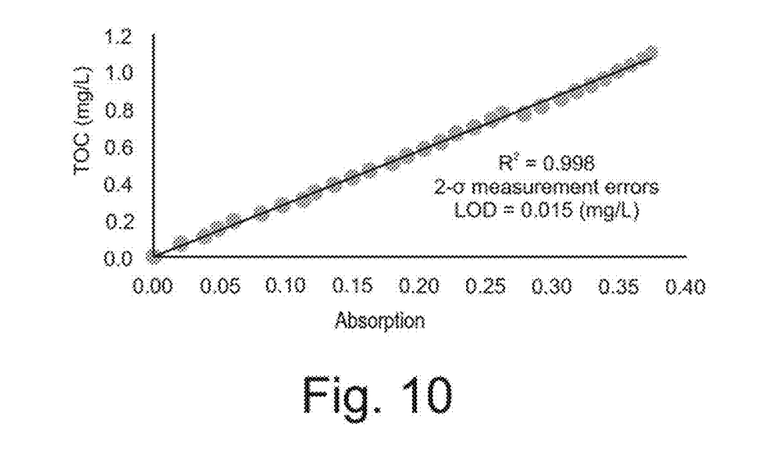

Results from use of the apparatus and method are illustrated in the performance graphs of FIGS. 8, 9, and 10. FIG. 8 is a graph of the measurements made employing an embodiment of the present invention. Airport runoff water was sampled during winter months when elevated levels of 50 to 5000 ppm were present due to aircraft deicing fluids. FIG. 9 is a graph of the measurements made employing an embodiment of the present invention to river water. FIG. 10 demonstrates ultra-high sensitivity to TOC. This level of detection for natural organic carbon (15 parts per billion) is unique for an all-optical instrument. This mapping curve was generated using 29 automated injection aliquots of the TOC standard potassium hydrogen phthalate (KHP).

The invention claimed is:

1. A method for the measurement of total organic carbon content in an aqueous stream comprising:
    measuring absorbance of electromagnetic energy by organic carbon in said aqueous stream in an optical sample cell at a wavelength of 190 nm ±10 nm, and
    calculating a value of total organic carbon in a computer executing stored instructions comprising:
    accepting said measured absorbance based only on measurements made at 190 nm ±10 nm,
    calculating concentration of organic carbon from Beer-Lambert Law based only on measurements made at 190 nm ±10 nm, and
    presenting from said calculated concentration a value of total organic carbon in human perceptible form.

2. The method of claim 1 wherein said measuring absorbance further comprises:
    directing an aqueous stream comprising a concentration of organic carbon through said optical sample cell;
    generating a first illumination probe of electromagnetic energy having a wavelength of 190 nm ±10 nm and directing said first illumination probe into an input port of said optical sample cell;
    detecting an intensity value of said first illumination probe from an output port of said optical sample cell, and
    storing said detected intensity value of said first illumination probe.

3. The method of claim 2 wherein said generating a first illumination probe further comprises pulsing said electromagnetic energy at a rate in a range of 10 pulses per second to 100 pulses per second.

4. The method of claim 2 wherein said degenerating a first illumination probe further comprises pulsing said electromagnetic energy for a pulse duration in the range of 0.4 μsec to 0.8 μsec.

5. The method of claim 2 wherein said detecting an intensity value further comprises detecting representations of electromagnetic photons and counting said detected representations of electromagnetic photons.

6. The method of claim 5 further comprising enabling said counting for the duration of a counting window.

7. The method of claim 6 wherein said counting window is substantially 10 msec.

8. The method of claim 6 wherein said calculating further comprises calculating a value of total organic carbon from said stored detected intensity value of said first illumination probe adjusted by said stored detected intensity value of said second illumination probe and said stored detected intensity value of said third illumination probe.

9. The method of claim 2 further comprising calibrating said optical sample cell, said calibrating comprising:
    directing an aqueous stream of pure water through said optical sample cell;

generating a second illumination probe of electromagnetic energy having a wavelength of 190 nm ±10 nm and directing said second illumination probe into said input port of said optical sample cell;

detecting an intensity value of said second illumination probe from said output port of said optical sample cell; and storing said detected intensity value of said second illumination probe.

10. The method of claim 9 wherein said calculating further comprises calculating a value of total organic carbon from said stored detected intensity value of said first illumination probe adjusted by said stored detected intensity value of said second illumination probe.

11. The method of claim 9 wherein said calibrating further comprises:

generating a third illumination probe of electromagnetic energy having a wavelength of 190 nm ±10 nm and directing said third illumination probe into said input port of said optical sample cell;

detecting an intensity value of said third illumination probe from said output port of said optical sample cell when an aqueous stream is absent from said optical sample cell; and storing said detected intensity value of said third illumination probe.

12. The method of claim 1 further comprising adjusting a path length over which absorbance of organic carbon in said aqueous stream is measured.

13. The method of claim 1 wherein said measuring absorbance further comprises directing said aqueous stream between a source of electromagnetic energy having a wavelength of 190 nm ±10 nm and an electromagnetic energy detector.

14. The method of claim 1 wherein said wavelength is one of substantially 193 nm and substantially 185 nm.

15. The method of claim 1 wherein the measuring further comprises:

generating electromagnetic energy at a wavelength between 180 nm and 1000 nm;

filtering said generated electromagnetic energy with an illumination filter tuned to pass electromagnetic energy having a wavelength of 190 nm ±10 nm to produce an illumination probe;

directing said illumination probe to an input port of said optical sample cell, whereby the aqueous stream is illuminated by said illumination probe;

reflecting said aqueous stream-illuminating illumination probe to re-illuminate said aqueous stream;

filtering said re-illuminating illumination probe that is output from an output port of said optical sample cell with a detection fiber tuned to pass electromagnetic energy having a wavelength of 190 nm ±10 nm; and detecting an intensity value of said re-illuminating illumination probe filtered by said detection filter.

16. An apparatus that measures total organic carbon content in an aqueous stream, comprising:

an electromagnetic energy generator that generates electromagnetic energy at a wavelength of 190 nm ±10 nm;

an optical sample cell through which the aqueous stream is routed;

an electromagnetic energy director that directs said generated electromagnetic energy into said optical sample cell and through said routed aqueous stream to produce an electromagnetic sample signal;

a bandpass filter, tuned to pass electromagnetic energy having a wavelength of 190 nm ±10 nm, and coupled to said optical sample cell to receive said electromagnetic sample signal;

a detector, coupled to said bandpass filter, to detect said electromagnetic sample signal at a wavelength of 190 nm ±10 nm; and a computer, coupled to said detector to calculate a value of total organic carbon from said detected electromagnetic sample signal.

17. The apparatus of claim 16 wherein said electromagnetic energy director further comprises a reflector disposed in said optical sample cell and arranged to reflect said generated electromagnetic energy into said routed aqueous stream.

18. The apparatus of claim 17 wherein said optical sample cell further comprises a piston upon which said reflector is disposed to adjust a path length of said generated electromagnetic energy through said routed aqueous stream.

19. The apparatus of claim 17 wherein said xenon-flash light source generates a pulsed light output at a pulsation rate in the range from 10 pulses per second to 100 pulses per second.

20. The apparatus of claim 16 wherein said electromagnetic energy generator further comprises a xenon-flash light source.

21. The apparatus of claim 16 wherein said electromagnetic energy generator further comprises a low pressure mercury light source that produces UV light substantially at a wavelength of 185 nm.

22. The apparatus of claim 16 further comprising an illumination bandpass filter disposed between said electromagnetic energy generator and said optical sample cell and tuned to pass electromagnetic energy having a wavelength of 190 nm ±10 nm.

23. The apparatus of claim 16 wherein said detector further comprises an electromagnetic photon representation detector.

24. The apparatus of claim 23 wherein said apparatus further comprises a counter coupled to said detector to count said electromagnetic photon representations detected by said detector and coupled to said computer to receive a command to open a counting window during which counts received from said detector are counted.

25. An apparatus that measures total organic carbon content in an aqueous stream comprising:

an electromagnetic energy generator that supplies pulsed electromagnetic energy to an optical sample cell at a pulse rate in the range from 10 pulses per second to 100 pulses per second and with a pulse width;

a computer coupled to and controlling said pulse rate of said electromagnetic energy generator;

an electromagnetic energy detector that receives said pulsed electromagnetic energy reflected from said optical sample cell that is diminished by an amount of energy absorption related to a concentration of organic carbon in the aqueous stream and that generates a representation of photon detections; and a counter that receives said detected representations of photons, that receives a gating command synchronized with said pulse rate from said computer to count detected representations of photons during a counting window, and that provides said count to said computer, whereby total organic carbon is calculated.

26. An apparatus that measures total organic carbon content in an aqueous stream comprising:

an electromagnetic energy generator that supplies pulsed electromagnetic energy to an optical sample cell at a pulse rate in the range from 10 pulses per second to 100 pulses per second and with a pulse width;

a computer coupled to and controlling said pulse rate of said electromagnetic energy generator;

an electromagnetic energy detector that receives said pulsed electromagnetic energy that is diminished by an amount of energy absorption related to a concentration of organic carbon in the aqueous stream and that generates a representation of photon detections; and a counter that receives said detected representations of photons, that receives a gating command synchronized with said pulse rate from said computer to count detected representations of photons during a counting window, and that provides said count to said computer, whereby total organic carbon is calculated wherein means are provided for (a) receiving the reflected photons by the detector, (b) transmitting a gating command synchronized with the pulse rate from the computer, and (c) providing the count to the computer.

* * * * *